US006781696B1

(12) United States Patent
Rosenberger et al.

(10) Patent No.: US 6,781,696 B1
(45) Date of Patent: Aug. 24, 2004

(54) APPARATUS AND METHOD FOR A MICROSPHERE WHISPERING-GALLERY MODE EVANESCENT-WAVE SENSOR

(75) Inventors: Albert T. Rosenberger, Stillwater, OK (US); Brian N. Strecker, Stillwater, OK (US)

(73) Assignees: The Board of Regents for Oklahoma State University, Stillwater, OK (US); Nomadics, Inc., Stillwater, OK (US)

( * ) Notice: Subject to any disclaimer, the term of this patent is extended or adjusted under 35 U.S.C. 154(b) by 0 days.

(21) Appl. No.: 10/313,905

(22) Filed: Dec. 6, 2002

Related U.S. Application Data

(63) Continuation of application No. 09/414,076, filed on Oct. 6, 1999, now abandoned.

(51) Int. Cl.[7] .............................................. G01N 21/59
(52) U.S. Cl. ...................................................... 356/437
(58) Field of Search ................................. 356/432, 437

(56) References Cited

U.S. PATENT DOCUMENTS

| | | | | |
|---|---|---|---|---|
| 5,445,964 A | * | 8/1995 | Lee et al. ...................... 436/60 |
| 5,835,231 A | | 11/1998 | Pipino ......................... 356/440 |
| 5,926,496 A | | 7/1999 | Ho et al. ...................... 372/92 |
| 5,943,136 A | | 8/1999 | Pipino et al. ............... 356/440 |
| 5,973,864 A | | 10/1999 | Lehmann et al. ........... 359/834 |
| 5,986,768 A | | 11/1999 | Pipino ......................... 356/440 |
| 6,009,115 A | | 12/1999 | Ho .............................. 372/92 |
| 6,097,555 A | | 8/2000 | Lehmann et al. ........... 359/834 |
| 6,172,823 B1 | | 1/2001 | Lehmann et al. ........... 359/834 |
| 6,172,824 B1 | | 1/2001 | Lehmann et al. ........... 359/834 |

OTHER PUBLICATIONS

Fehér, et al. "Optoacoustic trace–gas monitoring with near–infared diode lasers."*Applied Optics*, Mar. 20, 1994, vol. 33, No. 9, pp. 1655–1658.

Gabrysch, et al. "Simultaneous detection of CO and $Co_2$ using a semiconductor DFB diode laser at 1.578 $\mu m$." *Applied Physics B Lasers and Optics*, vol. 65, 1997, pp. 75–79.

(List continued on next page.)

*Primary Examiner*—Richard A. Rosenberger
(74) *Attorney, Agent, or Firm*—Fellers, Snider, Blankenship, Bailey & Tippens, P.C.

(57) ABSTRACT

A microsphere whispering-gallery mode evanescent-wave sensor for use in the detection and identification of atoms or molecules has been developed. In operation, the species under scrutiny is introduced proximate to a microsphere in which a whispering-gallery mode has been excited. The subject species then absorbs a portion of the microsphere's evanescent light energy at compound-specific wavelengths, which absorption is then used to detect and identify the subject species. Its concentration may be determined from the absorption signal on the light in reflection or transmission. High sensitivity in the instant invention results from the long effective absorption path length provided by the whispering-gallery mode's large Q which results in a detector that is suitable for use in trace-gas sensing. The instant microsphere detection system can rival the performance of a multipass cell and can be made part of a much more compact and rugged system. Among the many potential uses for the invention taught herein includes detection of carbon monoxide, carbon dioxide, and atmospheric trace gases such as methane and ammonia.

10 Claims, 4 Drawing Sheets

OTHER PUBLICATIONS

Ilchenko, et al. "Strain–Tunable High–$Q$ optical microsphere resonator." *Optics Communications*, vol. 145, 1998, pp. 86–90.

Littlejohn, et al. "Bent Silica Fiber Evanescent Absorption Sensors for Near–Infrared Spectroscopy." *Applied Spectroscopy*, vol. 53, No. 7, 1999, pp. 845–849.

Norris, D.J., Kuwata–Gonokami, M., and Moerner, W.E. Excitation of a single molecule on the surface of a spherical microcavity. *Applied Physics Letters*, vol. 71, No. 3, Jul. 21, 1997, pp. 297–299.

Pipino, A. C.R. Ultrasensitive surface spectroscopy with a miniature optical resonator. *Physical Review Letters*. vol. 83, No. 15, Oct. 11, 1999, pp. 3093–3096.

Pipino, A. C.R., Hudgens, J.W., and Huie, R.E. Evanescent wave cavity ring–down spectroscopy with a total–internal–reflection minicavity. *Review of Scientific Instruments*. vol. 68, No. 8, Aug. 1997, pp. 2978–2989.

Pipino, A. C.R., Hudgens, J.W. and Huie, R.E. Evanescent wave cavity ring–down spectroscopy for probing surface processes. *Chemical Physics Letters*. vol. 280, Nov. 28, 1997, pp. 104–112.

Vernooy, D. W., Furusawa, A., Georgiades, N.Ph., Ilchenko, V.S., and Kimble, H.J. Cavity QED with high–$Q$ whispering gallery modes. *Physical Review*. vol. 57, No. 4, Apr. 1998, pp. 57(4).

* cited by examiner

US 6,781,696 B1

APPARATUS AND METHOD FOR A MICROSPHERE WHISPERING-GALLERY MODE EVANESCENT-WAVE SENSOR

RELATED U.S. APPLICATION INFORMATION

This application is a continuation of application Ser. No. 09/414,076 filed on Oct. 6, 1999 abandoned.

TECHNICAL FIELD

This invention relates generally to the use of whispering-gallery (i.e., "WG" hereinafter) mode evanescent light waves to detect and/or identify chemical compounds and, more particularly, to the use of microspheres as optical evanescent-wave sensors for use in conjunction with molecular absorption spectroscopy.

BACKGROUND OF INVENTION

Molecular absorption spectroscopy is an analytical method that is premised on the observation that each chemical species preferentially absorbs certain wavelengths of incident light radiation. Further, the suite of light frequencies absorbed by a compound can often be used to uniquely identify it. Thus, spectrographic analysis of an unknown sample by exposing to light of different frequencies is a well known way of ascertaining the identity of that sample.

Laser spectroscopy is a variant of molecular absorption spectroscopy in which the incident light originates from a laser. In broadest terms, laser spectroscopy may be said to exploit the interaction between laser light and matter as a means of identifying the particular material that is present. Laser light far surpasses other light sources in brightness, spectral purity, and directionality. Further, if required, laser light can be produced in extremely intense and short pulses. The use of lasers can greatly increase the resolution and sensitivity of conventional spectroscopic techniques, such as absorption spectroscopy.

Of particular interest for purposes of the instant disclosure is the topic of optical evanescent-wave sensors and their use in absorption spectroscopy. As is well known to those skilled in the art, when light is incident on a medium at an angle of incidence that is greater than the critical angle, Snell's law suggests that all of the light will be reflected internally at that interface, i.e., total internal reflection. However, Fresnel's equations (in concert with Maxwell's equations) predict—and, in fact, it is observed in practice—that evanescent waves will be generated at the point of total reflection. The energy of this type of wave penetrates beyond the surface of the reflecting medium and returns to its original medium unless a second medium is introduced into the region of penetration of the evanescent wave. In other words, if another medium is brought near enough to the point where total internal reflection occurs, energy in the form of evanescent waves of the same frequency as the incident light will be transmitted to the alternative medium.

"Whispering-gallery" modes of light propagation are waves, with an evanescent component, that may be qualitatively described as traveling waves which move around a bent dielectric waveguide that closes upon itself (e.g., a sphere), with the energy confinement and guiding occurring by a physical mechanism not unlike total internal reflection in optical systems. These modes can have extremely low transmission losses, allowing such spheres to be used as microresonators with very high Q (i.e., quality factor), as was pointed out several years ago by Braginsky, Gorodetsky, and Ilchenko, "Quality-factor and nonlinear properties of optical WG modes," Phys. Lett. A, 137, 393 (1989), the disclosure of which is incorporated herein by reference. This observation has motivated a good deal of recent work in which WG mode microresonators have been used in or considered for experiments in such diverse subject matter areas as cavity quantum electrodynamics, nonlinear optics, laser stabilization, precision measurement of small displacements, and single-molecule excitation and emission.

If molecules are brought into proximity with a microsphere in which evanescent waves are propagating, the molecules will interact with those waves and attenuate them to the extent that these molecules would absorb the same wavelength in conventional light, i.e., absorption spectroscopy. Further, the high Q of the microsphere means that even a single atom or molecule interacting with a WG mode can potentially have a significant effect on the energy of that mode. Light resonance within the microsphere causes it to be much more sensitive than a conventional integrated-optical evanescent-wave sensor, thus making it ideal for use in absorption spectroscopy. However, heretofore there has been no effective way of exploiting the many useful properties of microsphere evanescent wave sensors for use in the detection and/or identification of chemical species.

Thus, what is needed is an absorption spectroscopy system that utilizes dielectric microspheres as optical evanescent-wave sensors (microsensors). This sort of device would benefit from the high quality factor of the WG modes of these microspheres and would potentially be orders of magnitude more sensitive than ordinary evanescent-wave sensors. Such microsensors will be able to detect single atoms or molecules, with sensitivities better than one part per billion. Accordingly, it should be recognized, as was recognized by the present inventor, that there exists, and has existed for some time, a very real need for a device that exhibits the various characteristics described above.

Before proceeding to a detailed description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMERY OF THE INVENTION

There is provided hereinafter a microsphere whispering-gallery mode evanescent-wave sensor for use in the detection and identification of atoms or molecules. In broadest terms, the instant invention consists of a microsphere into which WG mode light waves of a predetermined frequency have been introduced. When the microsphere is placed into contact with a sample, the WG mode evanescent light wave energy will interact with molecules of the sample and, if the wavelength of the WG mode matches an absorption band of the sample, the light energy emanating from the microsphere will be reduced. This approach can be used in a manner similar to conventional spectrographic analysis to identify a specific chemical compound. On the other hand, when no sample is present—or if the sample does not absorb light energy at the resonant frequency—and when the laser light frequency and microsphere resonant frequency are coincident, light will be emitted which is proportional in its power to the power of the input light. This effect may be used to establish a baseline emitted intensity at each light frequency.

According to a preferred embodiment of the instant invention, there is provided microsphere WG mode evanescent-wave sensor, wherein the frequency of the light within the microsphere is swept over a range of frequencies that encompasses a suspected absorption band of the sample. If the subject species absorbs light within the swept band, the microsphere's evanescent light energy will be attenuated at one or more compound-specific wavelengths, which attenuation is then used to detect and identify the subject species according to established spectroscopy principles. Further, the sample concentration can be determined by a comparison between the absorption-reduced signal and the light intensity at another non-absorbing frequency.

According to another preferred embodiment, there is provided a method and apparatus for use in absorption spectroscopy wherein a microsphere is subject to strain-induced changes in its resonant frequency. Preferably, the strain is introduced by way of a piezoelectric transducer, although other arrangements are certainly possible and have been contemplated by the inventor. The resonant frequency of the microsphere is systematically swept over a range which encompasses the frequency of the incident laser light and, when the source of light energy is in tune with the resonant frequency of the microsphere, transmission of evanescent energy to the microsphere occurs most favorably. Then, if a sample is introduced proximate to the microsphere and if it tends to absorb light at the resonant frequency, a decrease in the output of the evanescent light energy from the microsphere will be noted.

According to still another preferred embodiment, there is described hereinafter an invention substantially similar to that described previously, but wherein the frequency of the laser light is systematically varied around the (possibly strain-altered) resonant frequency of the microsphere. As before, the light energy emitted from the microsphere is monitored for a decrease in amplitude that would indicate a substance which absorbs light at that particular frequency.

By way of general explanation, the high sensitivity of the instant invention is due to the long effective absorption path length provided by the WG mode's large Q. This results in a detector that is suitable for use in, for example, trace-gas sensing. The instant microsphere detection system can rival the performance of a multipass cell and can be made part of a much more compact and rugged system. Among the many potential uses for the invention taught herein includes detection of carbon monoxide, carbon dioxide, and atmospheric trace gases such as methane and ammonia.

The foregoing has outlined in broad terms the more important features of the invention so that the detailed description that follows may be more easily understood, and so that the contribution to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

DETAILED DESCRIPTION

Technical Introduction

The so-called "whispering-gallery" modes of "transparent" dielectric spheres have extremely low transmission losses, allowing such spheres to be used as microresonators with very high quality factor Q, where Q is conventionally defined mathematically for a resonant microsphere as:

$$Q = \frac{v}{\Delta v},$$

where v is the frequency of the resonant light and $\Delta v$ is the frequency width over which the microsphere resonates. (Note that the term "transparent" should not be limited to visibly transparent, but should be understood to apply broadly to any material that is substantially transparent for a particular frequency of light). A WG mode is essentially the limiting case of propagation, by total internal reflection, around a great circle of the microsphere, as the number of reflections increases without bound. Similarly, the WG mode may be viewed as a surface-guided wave for which the circumference of the sphere is an integral number of wavelengths. This mode might either be the TE (i.e., transverse electric) component or the TM (transverse magnetic) component of the transmitted evanescent wave.

Figure 2A:
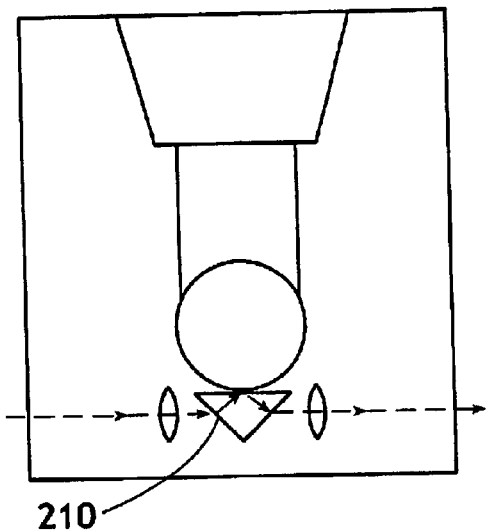
FIGS. 2A to 2D illustrates some preferred configurations of the microsphere system of the instant invention.
Figure 2B:
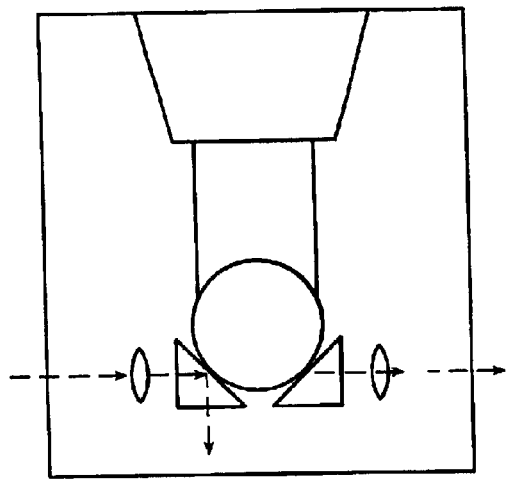
Figure 2C:
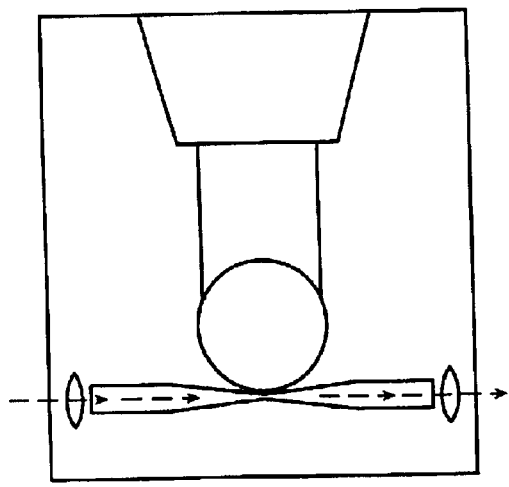
Figure 2D:
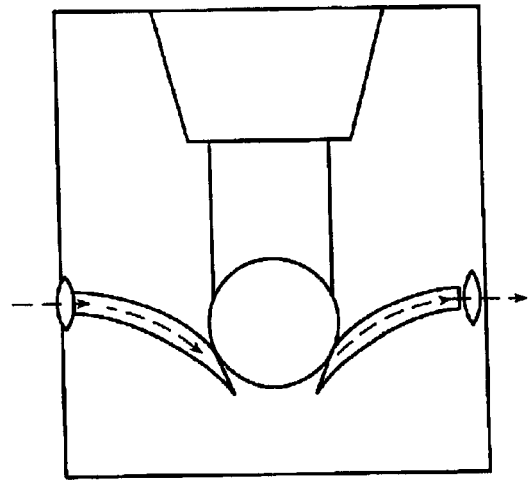
Figure 3A:
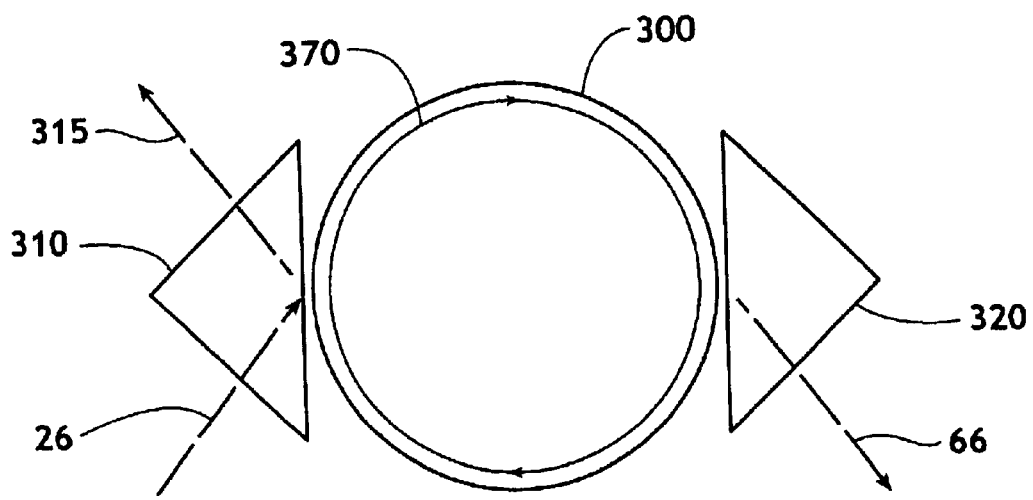
FIGS. 3A and 3B is a schematic illustration of how whispering-gallery mode waves can be transmitted into a microsphere via a prism and a tapered-fiber, respectively.

Coupling of laser light into and out of WG modes can be accomplished by frustrating the total internal reflection at a point on the sphere. In the preferred embodiment, this coupling is performed by using internal reflection in a prism whose surface is brought close to the microsphere, as is shown in FIGS. 2A, 2B, and 3A, or by overlapping the microsphere's evanescent field with that of an eroded or tapered single-mode optical fiber, as shown in FIGS. 2C, 2D, and, 3B.

Since the electromagnetic field of WG mode TM and TE waves is localized in the narrow and thin annular area near the equator of the microsphere, a compressive force that is applied at the "poles" of the microsphere will increase its effective radius without destroying its high Q properties. The resulting change in equatorial radius then changes the resonant frequency of the microsphere. One equation that may be used to relate the change in the radius of the microsphere to its resonant light frequency is:

$$v = \frac{cl}{2\pi n_{eff} a},$$

where, v is the frequency of the resonant laser light, c is the speed of light, R is the number of WG-mode wavelengths that "fit" around the (possibly stressed) microsphere, $n_{eff}$ is the index of refraction of the sphere, and a is the radius of the sphere at its equator. In the ideal case, the radius of the microsphere will be adjusted so that the previous equation is satisfied for the desired frequency v and a particular integer value of R, specifying the WG mode. This equation provides a general approach to the problem of adjusting the equatorial diameter of a stressed microsphere so that the WG mode wave produced thereby is practically optimal.

Fabrication of the Microsphere

In the preferred embodiment, the microsphere sensor will be constructed by melting the end of a thin unshielded optical fiber and allowing surface tension to draw the fused silica into a near-perfect sphere. This is preferably done using a hydrogen-oxygen mini-torch or a focused $CO_2$ laser beam. The size of a microsphere will usually be less than a millimeter or so in diameter, although it is to be expected that there will be some variation in the size according to the needs of the particular situation. In the preferred embodiment, the microspheres will be about 200–600 $\mu$m in diameter and be constructed from low-OH fused silica fibers. Additionally, each microsphere is normally left attached to its fiber stem, which can then be used for manipulation., although this is not required.

Preferred Apparatus

Figure 1:
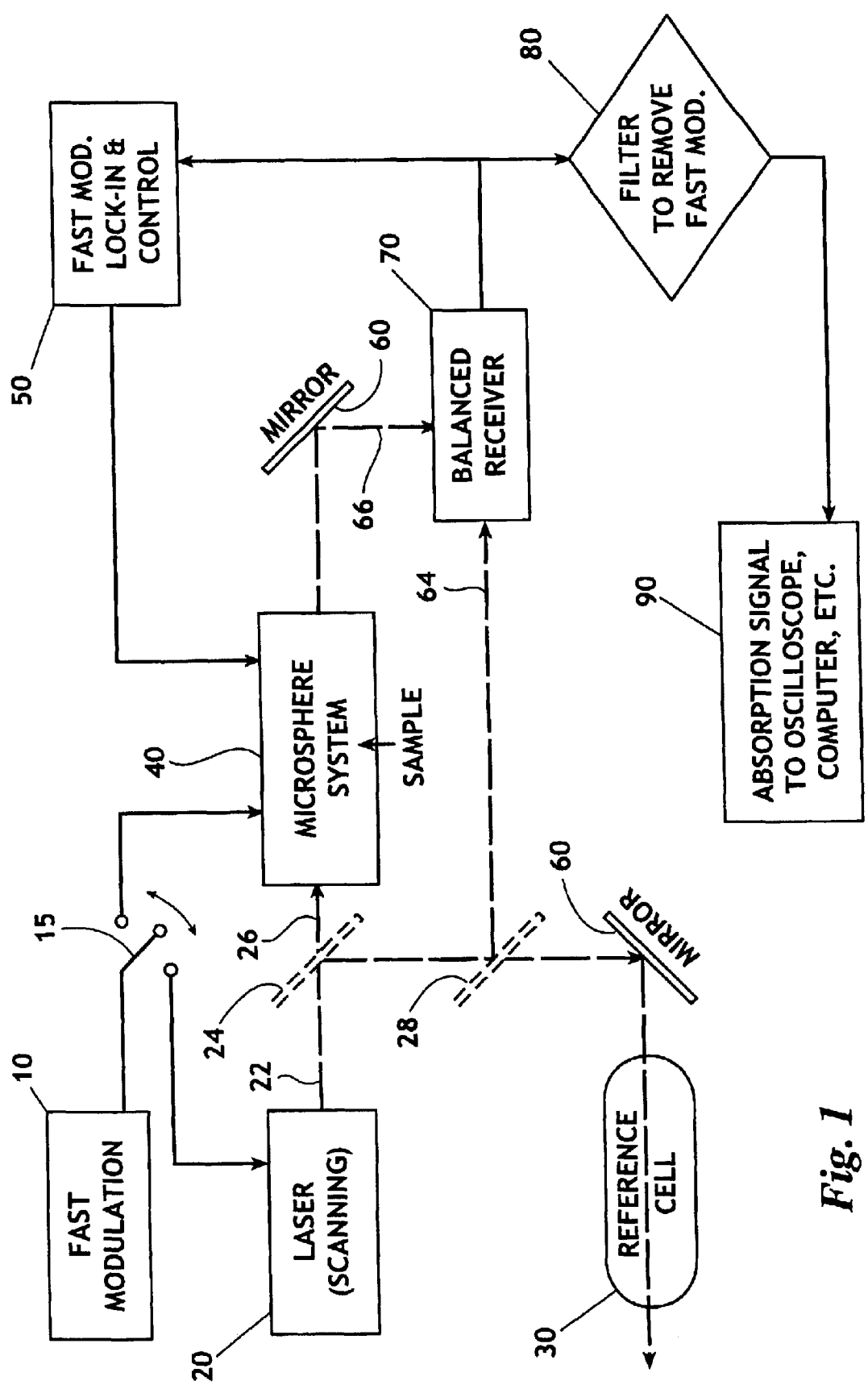
FIG. 1 contains a schematic diagram of a system suitable for use with the instant invention.

According to a first aspect of the instant invention, and as is illustrated in FIG. 1, there is provided a preferred apparatus for an absorption spectroscopy system, wherein a dielectric microsphere is used as optical evanescent-wave sensor. Laser 20 is, for reasons discussed later, preferably a tunable laser (or scanning laser) capable of lasing at a plurality of different wavelengths of light. It is not essential that the laser be tunable, though, as there are some applications where a laser that operates at a single light frequency would suffice. However, for purposes of this embodiment the laser 20 will be taken to be a laser that can emit light at a plurality of different wavelengths. Tunable coherent sources are available for any wavelength region from the far infrared into the ultraviolet and may be of many different types. Those skilled in the art will recognize that high-pressure molecular gas lasers, semiconductor diode lasers, spin-flip Raman lasers, and color-center lasers are among the many types of tunable lasers that would be suitable for use with the instant invention.

As can be seen in FIG. 1, the output 22 from laser 20 preferably passes through a beam splitter 24 which extracts a portion of the laser beam for use in a different portion of the apparatus. The remaining laser light 26 then enters microsphere system 40 which comprises the sensing component of the instant invention, four preferred variations of which are generally illustrated in FIGS. 2A to 2D. Note that reference cell 30 is an optional component of the instant invention and would generally be used to tune the laser output frequency to match an absorption wavelength of specific compound where, for example, only one compound is sought.

Figure 3B:
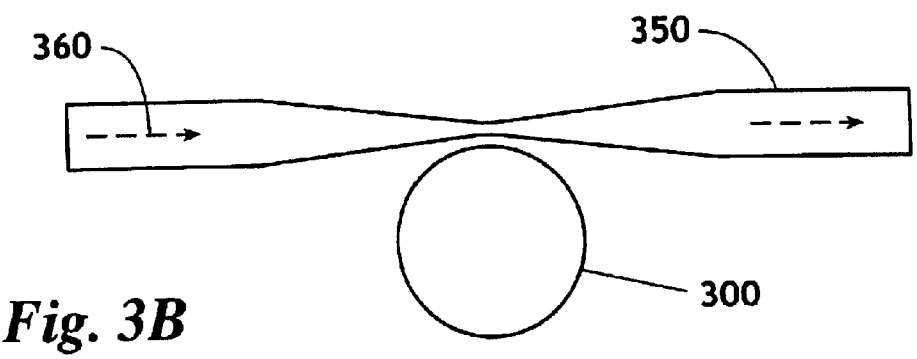

FIG. 3A contains a detailed illustration of a preferred arrangement of the basic microsphere sensing system 40. As is indicated in that figure, microsphere 300 is placed between—and proximate to—generating prism 310 and collecting prism 320. Incident laser light 26 is directed toward a point on the wall of the generating prism 310 adjacent to the microsphere 300. The light energy 26 strikes the wall at an angle which is beyond the critical and is, thus, largely reflected 315. Microsphere 300, because of its placement near the light reflection point, is the recipient of a transfer of evanescent energy from the laser beam 26. Evanescent energy that is transferred to the microsphere 300 propagates around its equator in the form of WG mode waves, which are schematically illustrated in FIG. 3A as circular rays 370. The wall of the collecting prism 320 nearest the microsphere 300 collects evanescent light energy, which then propagates out of the prism (schematically illustrated as light ray 66). Note that the collecting prism 320 is not strictly required, for example the embodiment of FIG. 2A utilizes a single prism 210. However, use of a second prism 320 eliminates the background present in the reflected light 315 that is due to the portion of the incident light 26 not coupled into the WG mode. Indeed, other variations of the instant invention do not utilize a prism of any sort: FIGS. 2C, 2D, and 3B illustrate other preferred arrangements in which light is coupled into and out of the WG mode using a tapered optical fiber or fibers.

Molecules that approach the surface of the microsphere 300 interact with the WG mode waves 370, reducing the energy in those waves if the molecule absorbs light at the frequency of the wave. Thus, the amplitude of the light energy 66 that is subsequently released from the prism 320 is indicative of the species of the sample.

Figure 4:
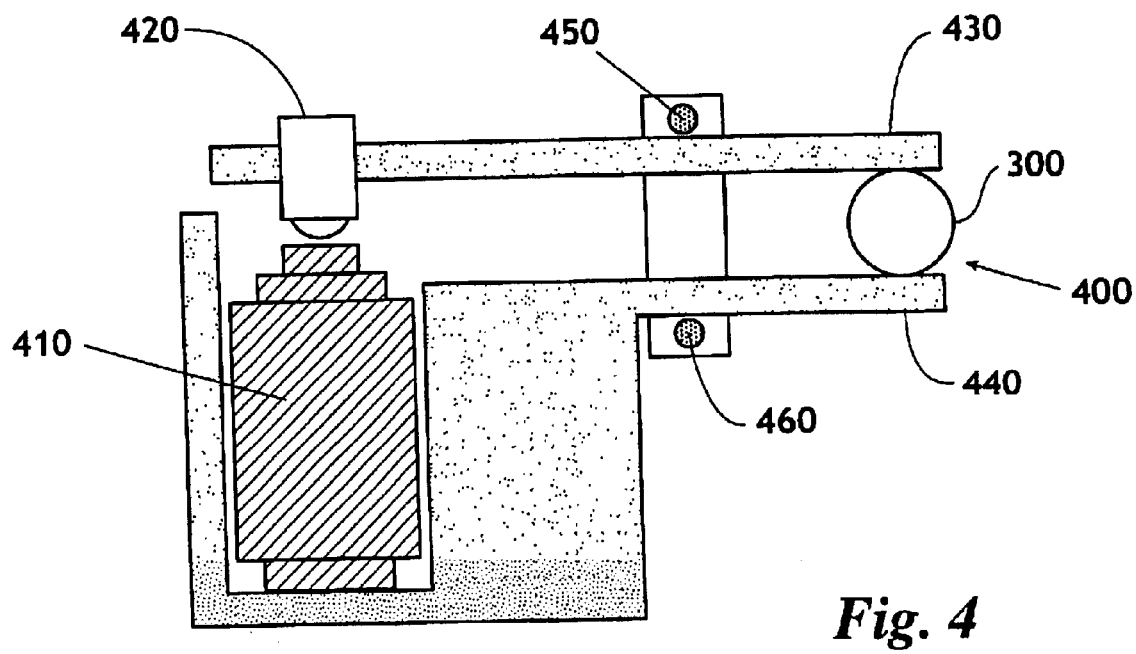
FIG. 4 contains a preferred arrangement of the device used to tune the microsphere resonance frequency.
Figure 5:
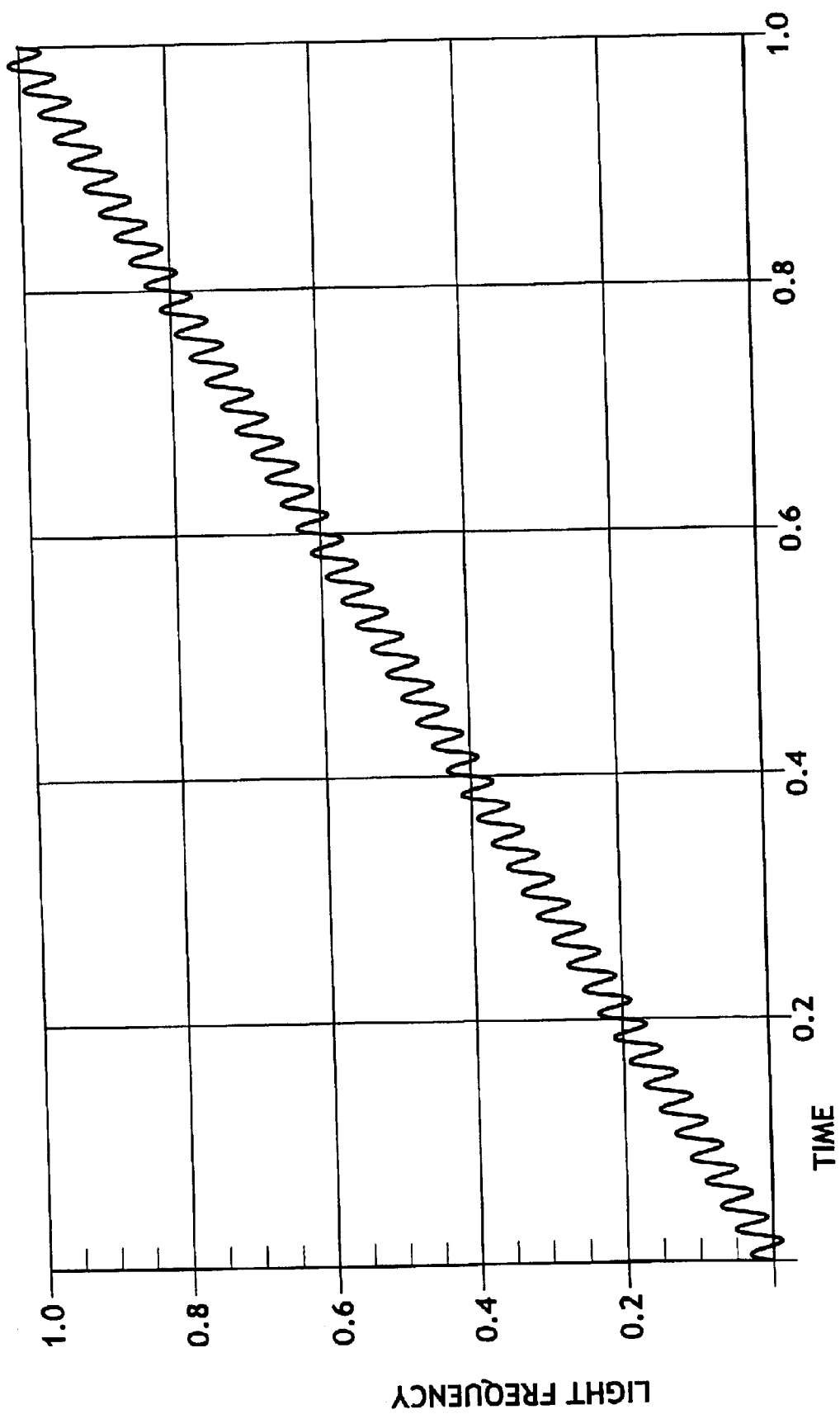
FIG. 5 illustrates in a general way the net result of superimposing a fast modulation signal on the slower tuned laser light frequency change.

FIG. 4 contains a cross-sectional view of a preferred embodiment of a device 400 for adjusting the microsphere resonance frequency by compression. As was discussed previously, compressing the sphere 300 adjusts its resonant frequency through a free spectral range and means that the sphere can be kept generally in resonance with the laser light as the laser 20 is tuned. As is illustrated generally in FIG. 4, the microsphere compression system 400 preferably holds the microsphere 300 between two arms: an lower stationary arm 440 and an upper lever arm 430. The upper lever arm 430 is made to bear down on the microsphere 300 through application of an upward force from piezoelectric device 410, which presses against pad 420. Pad 420 is affixed to upper lever arm 430 so that pressure against the pad 420 is translated into compressive force through leverage against pins 450 and 460. In the event that the laser 20 is a scanning laser, the compression system 400 will generally track the frequency of the tuned laser light 26, continuously changing the pressure placed on the microsphere 300 so as to keep its resonant frequency matched with the frequency of the incident laser light.

Returning to FIG. 1, the light energy 66 that is emitted from the microsphere system 40 is next passed to balanced receiver 70. The balanced receiver 70 uses a portion 64 of the original laser signal 22 (as preferably obtained via beams splitters 24 and 28) to correct the output signal 66 for variations in the strength of the input signal 22. Absent such a correction, input signal strength variations could easily be confused with variations in output intensity due to molecular absorption. Further, since the magnitude of the signal drop attributable to absorption by the sample might amount to only 2% or so of the input signal 26, it is preferable to remove the overall effect of the source so that the remaining signal can be examined against a background of nearly "zero" rather than against a background which is at the base level of the input signal 24. The balanced receiver 70 preferably performs all of these functions.

Output from the balanced receiver 70 is next preferably sent to filter 80, which is designed to remove the effects of the induced "fast" modulation, which is described hereinafter. In brief, this device 80 smoothes the output signal by the amplitude modulation that has been introduced by fast frequency modulation of the laser 20 or microsphere compression device 400. This device 80 could either be a hardware notch-type filter or a filter implemented in software. But in the preferred embodiment, the filter 80 will be implemented in hardware.

Finally, the signal after filtering is ready for subsequent analysis 90 by, for example, oscilloscope or computer.

Analysis of the output signal essentially consists of an examination of the signal to determine if the light output 66 at one or more light frequencies is attenuated with respect to the light output at other frequencies. Further, the ratio of signals between light intensities at and away from molecular resonance frequencies can be used to estimate the molecular concentration of the sample according to methods well known to those skilled in the art.

As is illustrated in FIG. 1, a portion of the output from the balanced receiver 70 is preferably fed back into fast modulation lock-in and control module 50, the "control module" 50 hereinafter. In brief, this module is designed to recognize when optical resonance occurs within the microsphere 300 and hold the stress unit 400 at that pressure when it occurs by feeding back to the dc level of the stress unit 400. This will tend to keep the microsphere 300 in tune with the current scanned laser frequency. The control module 50 accomplishes this by phase-sensitive detection of the amplitude modulation, of the emitted light 66, that results from the action of the fast modulation unit 10. In both operating modes/embodiments described below, the laser frequency and WG mode resonance curve are moved relative to each other, but so slightly that the control module 50 can keep the microsphere precisely resonant with the slowly scanning laser. When the resonant frequency of the microsphere matches the laser frequency, the light energy emitted from the microsphere 300 will be at a maximum.

Fast modulation unit 10 is designed to operate in one of two modes: as a controller of the laser 20 signal or as a controller of the microsphere compression system 400. (Hence, the "switched" connection 15 in FIG. 1). Although FIG. 1 suggests the use of a single fast modulation unit 10 which is switched between the laser 20 and stress unit 400, clearly two separate units could be utilized instead. When connected to the laser 20, the fast modulation unit 10 operates by superimposing a small-amplitude kilohertz modulation on the changing frequency of the laser light. When the device 10 is connected to the compression system 400, it modifies the signal that drives the piezoelectric device 410 to similarly superimpose a fast small-amplitude modulation on top of the compression signal that keeps the resonant frequency of the microsphere 300 generally in tune with that of the laser. In the preferred embodiment, fast modulation unit 10 provides as an output a voltage which varies rapidly and regularly in time. For example, in the preferred embodiment, the modulation unit 10 cycles at about a kilohertz. This will typically be a very rapid oscillation in comparison to the cycle speed of the scanning laser (which might be as slow as a few Hertz).

According to a first preferred embodiment, the fast modulation unit 10 will be placed into communication with the microsphere stress unit 400. In that case, as the relatively slow tunable laser 20 tracks over its range of light frequencies, the fast modulation unit 10 operates to cause the stress unit 400 to sweep the microsphere resonance profile over a narrow range about the current laser 20 output frequency.

In another embodiment, the fast modulation unit 10 is situated so as to be in communication with scanning laser 20, rather than the stress unit 400. In this embodiment, the laser 20 will generally be driven to oscillate through a predetermined frequency range as before. Also as before, the stress unit 400, which is controlled by module 50, will systematically stress the microsphere 300 so that its resonant frequency precisely tracks the frequency of the laser. However, in this embodiment the fast modulation unit 10 will superimpose an oscillation on top of the slower laser frequency to vary it as so encompass the resonant frequency of the microsphere 300.

Sensitivity

In any of the forms that the instant invention takes (e.g., FIGS. 2 and 3), a simple model of the microsphere describes it as a ring resonator, where the prism or fiber coupling is treated as a partially-transmitting mirror of reflectivity $r^2$. This reflectivity can be varied by changing the specifics of the coupling, such as the prism-sphere separation. In this simple model, r is assumed to be real and the incident light is assumed to have a frequency resonant with the fundamental whispering-gallery mode of the microsphere. These assumptions do not limit the generality of the conclusions that follow, as will be recognized by those skilled in the art. The Q of the microsphere is determined by several different types of losses, but for the purposes of this model Q can be attributed to an internal loss specified by the effective absorption coefficient $\alpha_i$. Then Q is given by $$Q = \frac{2\pi n_{\mathit{eff}}}{\alpha_i \lambda},$$

where $n_{\mathit{eff}}$ is the sphere's index of refraction and $\lambda$ is the wavelength of the incident light. It is further assumed (again without restriction of generality) that the frequency of the incident light also coincides with a homogeneously broadened resonant absorption of the atom that we wish to detect. Here and below, "atom" is used as a generic term for the species (atom, molecule, etc.) to be detected. Now if there are atoms in the evanescent part of the mode, the absorption coefficient will change to $\alpha = \alpha_i + \alpha_a$, where $\alpha_a$ is the resonant absorption coefficient of the atom, given by $$\alpha_a = \frac{\lambda^2 N}{4\pi^2 \tau_{sp} \Delta v},$$

where N is the number density of resonant atoms, $\tau_{sp}$ is their spontaneous lifetime, and $\Delta v$ is their absorption line width.

The fraction of the incident intensity that is reflected from the microsphere (e.g., 315 in FIG. 3A) is R; and the fraction transmitted through the microsphere (e.g., 66 in FIG. 3A) is T. Either of these quantities constitutes the detectable signal. The reflected and transmitted fraction can be shown to be equal to $$R = \left(\frac{1-x+a}{1+x+a}\right)^2,$$

$$T = \left(\frac{2x}{1+2x+a}\right)^2,$$

where, $$a = \frac{\alpha_a}{\alpha_i}, \text{ and } x = \frac{1-r^2}{\alpha_i L}$$

L being the circumference of the sphere. For low atomic density (a<<1), the expressions for T and R can each be written as proportional to the factor $\exp[-\alpha_a L_{\mathit{eff}}]$. Here, $L_{\mathit{eff}}$ is the effective absorption path length, which can be as large as $2/\alpha_i$ in the under-coupled case (x<<1). For a sphere with $n \cong 1.5$, and using $\lambda \cong 1$ μm, the first equation presented previously becomes $$Q \approx \frac{10^5 \text{ cm}^{-1}}{\alpha_i};$$

for Q~$10^8$, we have $\alpha_i$~$10^{-3}$ cm$^{-1}$. Thus, depending on the specifics, $L_{eff}$ can be on the order of tens of meters.

Model calculations have been done using CO as a test case, for comparison with previously reported results from a 30-cm multipass-cell sensor with an effective detection path length of about 100 meters. The high Q (about $10^8$) of the instant microsensor 300 means that its effective detection path length can also be about 100 meters. (However, the microsphere has the advantage of being much smaller than the multipass cell, and fiber-optic coupling can be used; a much more compact sensor head can therefore be engineered, at a substantially lower cost, and with much less critical alignment tolerances.) Using direct absorption measurements, a sensitivity of one part in $10^9$ thus appears feasible, but it should be possible to do much better. The microsensor can be used just as well for the detection of other atmospheric and biogenic trace gases (e.g., $CO_2$, $NH_3$, $CH_4$, NO, $N_2O$, $C_2H_6$, $H_2S$, $H_2CO$, $SO_2$, HF, HCl, etc.).

Additional Embodiments

It should be noted at the outset that in its simplest form, the instant invention could involve only a fixed frequency laser in combination with a single, uncompressed microsphere that has been chosen to resonate at the exact frequency of the laser. This setup could be used for the very restricted purpose of determining whether or not a specific absorption band was present in a sample. Where a specific compound is sought (e.g., in the case of certain pollutants), this arrangement could prove to be an ideal solution.

Additionally, the instant inventor has specifically contemplated that the instant invention might be augmented by additional features such as the use of a broad-band light source (e.g., an L.E.D.) which may be preferable when the compound to be detected has a broad absorption band. Further, it should be possible to improve the results presented herein by controlling the effects of environmental fluctuations, mechanical and thermal noise, and surface contamination.

Still further, the technique of using a strain-tuned microsphere could be extended into the mid-infrared, making use of new tunable semiconductor lasers currently being perfected. In this spectral region, comprising wavelengths from 2 to 8 $\mu$m, another four to five orders of magnitude in sensitivity can be gained because of the much greater strength of fundamental (rather than overtone or combination-band) ro-vibrational transitions. The optics of this spectral region is not as well understood, so the microsphere fabrication and coupling will need to be developed, using new types of mid-IR-transmitting glasses. Even further, the scanning technique described earlier could be changed to a somewhat faster modulation of the wavelength, scanning back and forth across the molecular resonance, and then detecting the derivative of the signal. This wavelength modulation spectroscopy can improve the sensitivity by another two to three orders of magnitude.

Additionally, although the entire disclosure has been directed toward a discussion of the use of a microsphere as an evanescent-wave sensor, other shapes could alternatively be used. For example, those skilled in the art will recognize that a "disk" shape could be substituted in place of the microsphere, with the resonance frequency adjusted according to principles familiar in the industry.

Whispering-gallery microsensors have the potential for many other uses in addition to the detection of atmospheric gases. They can also be used for partial pressure measurement in vacuum systems, replacing mass spectrometers. They can be immersed, and so have the potential to be used for the characterization of liquid environments as well, ranging from marine sensing applications to contaminant monitoring in jet fuel. In addition, it is also possible that, by coating the microspheres, sensitivity to biological and chemical warfare agents, and perhaps even use in DNA sequencing, can be achieved.

While the inventive device has been described and illustrated herein by reference to certain preferred embodiments in relation to the drawings hereto attached, various changes and further modifications, apart from those shown or suggested herein, may be made by those skilled in the art, without departing from the spirit of the inventive concept, the scope of which is to be determined by the following claims.

References

The documents that are listed hereinafter are specifically incorporated by reference into this patent application.

[1] V. B. Braginsky, M. L. Gorodetsky, and V. S. Ilchenko, "Quality factor and nonlinear properties of optical whispering-gallery modes," Phys. Lett. A 137, 393–397 (1989).

[2] V. B. Braginsky, M. L. Gorodetsky, V. S. Ilchenko, and S. P. Vyatchanin, "On the ultimate sensitivity in coordinate measurements," Phys. Lett. A 179, 244–248 (1993).

[3] V. S. Ilchenko, M. L. Gorodetsky, and S. P. Vyatchanin, "Coupling and tunability of optical whispering-gallery modes: a basis for coordinate meter," Opt. Commun. 107, 41–48 (1994).

[4] D. J. Norris, M. Kuwata-Gonokami, and W. E. Moemer, "Excitation of a single molecule on the surface of a spherical microcavity," Appl. Phys. Lett. 71, 297–299 (1997).

[5] M. D. Barnes, N. Lenner, C.-Y. Kung, W. B. Whitten, J. M. Ramsey, and S. C. Hill, "Real-time observation of single-molecule fluorescence in microdroplet streams," Opt. Lett. 22, 1265–1267 (1997).

[6] S. Arnold, S. Holler, N. L. Goddard, and G. Griffel, "Cavity-mode selection in spontaneous emission from oriented molcules in a microparticle," Opt. Lett. 22, 1452–1454 (1997).

[7] M. L. Gorodetsky and V. S. Ilchenko, "High-Q optical whispering-gallery microresonators: precession approach for spherical mode analysis and emission patterns with prism couplers," Opt. Conmmun. 113, 133–143 (1994).

[8] N. Dubreuil, J. C. Knight, D. K. Leventhal, V. Sandoghdar, J. Hare, and V. Lefevre, "Eroded monomode optical fiber for whispering-gallery mode excitation in fused-silica microspheres," Opt. Lett. 20, 813–815 (1995).

[9] A. Serpengüzel, S. Arnold, G. Griffel, and J. A. Lock, "Enhanced coupling to microsphere resonances with optical fibers," J. Opt. Soc. Am. B 14, 790–795 (1997).

[10] E. F. Schipper, R. P. H. Kooyman, A. Borreman, and J. Greve, "The Critical Sensor: A New Type of Evanescent-Wave Immunosensor," Biosensors & Bioelectronics 11, 295–304 (1996), and references therein.

[11] L. A. Orozco, A. T. Rosenberger, and H. J. Kimble, "Optical Bistability in the Mixed Absorptive-Dispersive Regime with Two-State Atoms," Phys. Rev. A 36, 3248–3252 (1987).

[12] L. A. Orozco, H. J. Kimble, A. T. Rosenberger, L. A. Lugiato, M. L. Asquini, M. Brambilla, and L. M.

Narducci, "Single-Mode Instability in Optical Bistability," Phys. Rev. A 39, 1235–1252 (1989).

[13] A. T. Rosenberger, L. A. Orozco, H. J. Kimble, and P. D. Drummond, "Absorptive Optical Bistability in Two-State Atoms," Phys. Rev. A 43, 6284–6302 (1991).

[14] A. T. Rosenberger and Jeong-Mee Kim, "Transit-Induced Optical Multistability," Opt. Commun. 101, 403–410 (1993).

[15] Jeong-Mee Kim and A. T. Rosenberger, "Detuning Effects in Transit-Induced Optical Multistability," Opt. Commun. 115, 401–410 (1995).

[16] T. V. Sarkisyan, A. N. Oraevsky, A. T. Rosenberger, R. L. Rolleigh, and D. K. Bandy, "Nonlinear Gain and Carrier Temperature Dynamics in Semiconductor Laser Media," J. Opt. Soc. Am. B 15, 1107–1119 (1998).

[17] T. Töpfer, K. P. Petrov, Y. Mine, D. Jundt, R. F. Curl, and F. K. Tittel, "Room-temperature mid-infrared laser sensor for trace gas detection," Appl. Opt. 36, 8042–8049 (1997).

[18] M. Gabrysch, C. Corsi, F. S. Pavone, and M. Inguscio, "Simultaneous detection of CO and $CO_2$ using a semiconductor DFB diode laser at 1.578 $\mu$m," Appl. Phys. B 65, 75–79 (1997).

[19] M. Fehér, Y. Jiang, J. P. Maier, and A. Miklós, "Optoacoustic trace-gas monitoring with near-infrared diode lasers," Appl. Opt. 33, 1655–1658 (1994).

[20] K. Uehara, "Dependence of harmonic signals on sample-gas parameters in wavelength-modulation spectroscopy for precise absorption measurements," Appl. Phys. B 67, 517–523 (1998).

[21] V. S. Ilchenko, P. S. Volikov, V. L. Velichansky, F. Treussart, V. Lefèvre-Seguin, J.-M. Raimond, and S. Haroche, "Strain-tunable high-Q optical microsphere resonator," Opt. Commun. 145, 86–90 (1998).

[22] M. Fehér and P. A. Martin, "Tunable diode laser monitoring of atmospheric trace gas constituents," Spectrochimica Acta A 51, 1579–1599 (1995).

[23] P. Werle, "A review of recent advances in semiconductor laser based gas monitors," Spectrochimica Acta A 54, 197–236 (1998).

[24] J. Wasylak, M. Laczka, and J. Kucharski, "Glass of high refractive index for optics and optical fiber," Opt. Eng. 36, 1648–1651 (1997).

[25] J. Wasylak, "New glasses of shifted absorption edge in infrared as materials for optics and light fiber technique," Opt. Eng. 36, 1652–1656 (1997).

[26] J. S. Sanghera and I. D. Aggarwal, "Development of chalcogenide glass fiber optics at NRL," J. Non-Cryst. Solids 213 & 214, 63–67 (1997).

What is claimed is:

1. A method of determining whether a sample absorbs light at a particular light frequency, comprising the steps of:
   (a) exciting a whispering-gallery light mode within a sensor at said particular light frequency;
   (b) exposing said sensor to said sample, thereby producing a responsive intensity at which said sensor reflects or transmits light; and,
   (c) determining, using at least said responsive intensity, whether said sample absorbs light at said particular frequency.

2. A method of determining whether a sample absorbs light at a particular light frequency according to claim 1, wherein said sensor of step (a) is a microsphere sensor.

3. A method of determining whether a sample absorbs light at a particular frequency according to claim 1, wherein step (a) includes the steps of:
   (a1) directing laser light at a transparent material so as to create an evanescent wave therein,
   (a2) positioning said sensor proximate to said transparent material so that said evanescent wave of said transparent material overlaps an evanescent portion of a whispering-gallery mode of said sensor.

4. A method according to claim 3, wherein said transparent material is a prism.

5. A method according to claim 3, wherein said transparent material is an optical fiber.

6. A method according to claim 1, wherein said sensor of step (a) reflects or transmits light at an initial intensity.

7. A method according to claim 6, wherein step (c) includes the step of:
   (c1) determining by using at least said initial intensity and responsive intensity, whether said sample absorbs light at said particular frequency.

8. A microsphere whispering-gallery mode evanescent-wave sensor comprising:
   (a) a tunable laser, said tunable laser being capable of emitting laser light at a plurality of light wavelengths;
   (b) a microsphere sensor, said tunable laser being positionable to emit laser light toward said microsphere sensor and said microsphere sensor emitting at least a portion of said laser light therefrom;
   (c) a microsphere compression system, said microsphere compression system acting to compress said microsphere along a polar axis;
   (d) a fast modulation unit in electronic communication with at least one of said tunable laser and said microsphere compression system, said fast modulation unit imposing a high frequency oscillation on; and,
   (e) a fast modulation lock-in and control unit, said fast modulation lock-in and control unit sensing at least a portion of said light emitted from said microsphere and acting to cause said microsphere compression system to compress said microsphere in concert with a light frequency emitted by said tunable laser.

9. A method of determining whether a sample absorbs light at a particular light frequency, comprising the steps of:
   (a) exciting a whispering-gallery light mode within a sensor at said particular light frequency utilizing a broad-band light source;
   (b) exposing said sensor to said sample, thereby producing a responsive intensity at which said sensor reflects or transmits light; and,
   (c) determining, using at least said responsive intensity, whether said sample absorbs light at said particular frequency.

10. A method according to claim 9, wherein said broad-band light source is an LED.

* * * * *

UNITED STATES PATENT AND TRADEMARK OFFICE
CERTIFICATE OF CORRECTION

PATENT NO. : 6,781,696 B1
DATED : August 24, 2004
INVENTOR(S) : Albert T. Rosenberger et al.

It is certified that error appears in the above-identified patent and that said Letters Patent is hereby corrected as shown below:

Column 2,
Line 46, change "SUMMERY" to -- SUMMARY --

Column 4,
Line 56, $v = \dfrac{cl}{2\pi n_{eff} a}$, change to $v = \dfrac{cR}{2\pi n_{eff} a}$, Column 5,
Line 18, change "manipulation.," to -- manipulation, --

Column 6,
Line 54, change "level of the input signal 24." to -- level of the input signal 26. --

Signed and Sealed this

Twenty-fourth Day of May, 2005

JON W. DUDAS
*Director of the United States Patent and Trademark Office*